(12) United States Patent
Colucci

(10) Patent No.: US 8,262,750 B2
(45) Date of Patent: Sep. 11, 2012

(54) METHOD FOR PRODUCING POLYOLEFINIC AMINES AND COMPOSITIONS CONTAINING SAME

(75) Inventor: William Jay Colucci, Glen Allen, VA (US)

(73) Assignee: Afton Chemical Corporation, Richmond, VA (US)

( * ) Notice: Subject to any disclaimer, the term of this patent is extended or adjusted under 35 U.S.C. 154(b) by 472 days.

(21) Appl. No.: 12/496,507

(22) Filed: Jul. 1, 2009

(65) Prior Publication Data
US 2010/0000147 A1    Jan. 7, 2010

Related U.S. Application Data

(62) Division of application No. 11/426,195, filed on Jun. 23, 2006, now abandoned.

(51) Int. Cl.
C10L 1/22       (2006.01)
C10L 10/04      (2006.01)
C08F 36/06      (2006.01)
C08F 10/06      (2006.01)
C07C 215/06     (2006.01)

(52) U.S. Cl. ........... 44/412; 44/418; 44/640; 525/333.2; 525/333.7; 564/355

(58) Field of Classification Search .............. 44/412, 44/418, 640; 525/333.2, 333.7; 564/355
See application file for complete search history.

(56) References Cited

U.S. PATENT DOCUMENTS

| 4,832,702 | A |   | 5/1989 | Kummer et al. |         |
|-----------|---|---|--------|---------------|---------|
| 4,946,982 | A | * | 8/1990 | Johnson       | 560/158 |
| 5,752,990 | A | * | 5/1998 | Siskin et al. | 44/418  |
| 6,387,837 | B1| * | 5/2002 | Dauben et al. | 502/87  |

OTHER PUBLICATIONS

Vyakaranam, K., et al., "$Li^+$—Catalyzed Radical Polymerization of Simple Terminal Alkenes," *J. Am. Chem. Soc. 128*: 5610-5611, American Chemical Society, US (2006).
Office Action mailed on Apr. 2, 2009 in U.S. Appl. No. 11/426,195, William Jay Colucci, filed on Jun. 23, 2006.

* cited by examiner

*Primary Examiner* — James O Wilson
*Assistant Examiner* — Ebenezer O Sackey
(74) *Attorney, Agent, or Firm* — Thomas & Karceski, P.C.

(57) ABSTRACT

Polyolefinic amines may be produced in a reaction comprising contacting an olefin or a polyolefin with an azo compound under free radical conditions to form a polyolefinic nitrile having an average molecular weight of at least 250, followed by reducing the polyolefinic nitrile to a corresponding polyolefinic amine. The polyolefinic amines produced by the reaction may be included as a detergent in compositions, such as fuel compositions, additive compositions, and/or carrier compositions.

18 Claims, No Drawings

METHOD FOR PRODUCING POLYOLEFINIC AMINES AND COMPOSITIONS CONTAINING SAME

The present application is a divisional of U.S. patent application Ser. No. 11/426,195, filed Jun. 23, 2006 now abandoned.

BACKGROUND OF THE INVENTION

1. Field of the Invention

This invention relates to a reaction for producing polyolefinic amines comprising contacting an olefin or a polyolefin with an azo compound under free radical conditions to form a polyolefinic nitrile having an average molecular weight of at least 250, followed by reducing the polyolefinic nitrile to the corresponding polyolefinic amine. The polyolefinic amines produced by the reaction may be included as a detergent in compositions, such as fuel compositions, additive compositions, and/or concentrate compositions.

2. Background Art

The use of conventional fuels without detergent and corrosion-inhibiting additives promotes the accumulation of deposits in the engine resulting from the presence of polar aromatic compounds and traces of lubricants.

The accumulation of deposits has a detrimental effect on the quality of evaporation of the fuel, which causes an increase in consumption, an increase in the emission of pollutants and of smoke, which is significantly greater during acceleration, and, finally, an increase in noise.

To overcome this problem of fouling of the engine, it is possible to periodically clean the fouled components and particularly the injectors but, in the long run, this method becomes very expensive.

Another method for reducing fouling by deposits in engines is to utilize detergents that are capable of being adsorbed on the metal surfaces to prevent the formation of deposits and/or to remove the deposits already formed. Polyolefinic amines may be used as detergents to prevent the formation of deposits and/or to remove the deposits already formed.

A need continues to exist in the art for methods of producing polyolefinic amines in an efficient and cost-effective manner.

BRIEF SUMMARY OF THE INVENTION

Polyolefinic amines may be produced by a reaction comprising contacting an olefin or a polyolefin with an azo compound under free radical conditions to form a polyolefinic nitrile having an average molecular weight of at least 250, followed by reducing the polyolefinic nitrile to a corresponding polyolefinic amine. The polyolefinic amines produced by the reaction may be included as detergents in compositions, including fuel compositions, additive compositions, and/or concentrate compositions.

In one aspect, the disclosure herein is directed to a process for producing polyolefinic amines having an average molecular weight of at least 250 by polymerizing an olefin in a reaction that comprises contacting the olefin with an azo compound under free radical conditions to form a polyolefinic nitrile having an average molecular weight of at least 250, followed by reducing the polyolefinic nitrile to a corresponding polyolefinic amine.

In another aspect, the disclosure herein is directed to a process for producing polyolefinic amines having an average molecular weight of at least 250 by adding an amine functional group to a polyolefin in a reaction comprising contacting a polyolefin with an azo compound under free radical conditions to form a polyolefinic nitrile having an average molecular weight of at least 250, followed by reducing the polyolefinic nitrile to a corresponding polyolefinic amine.

In yet another aspect, the disclosure herein is directed to compositions comprising, or consisting essentially of, polyolefinic amines having an average molecular weight of at least 250 produced by a reaction comprising contacting an olefin or a polyolefin with an azo compound under free radical conditions to form a polyolefinic nitrile having an average molecular weight of at least 250, followed by reducing the polyolefinic nitrile to a corresponding polyolefinic amine.

In still yet another aspect, the disclosure herein is directed to fuel compositions comprising, or consisting essentially of, polyolefinic amines having an average molecular weight of at least 250 produced by a reaction comprising contacting an olefin or a polyolefin with an azo compound under free radical conditions to form a polyolefinic nitrile having an average molecular weight of at least 250, followed by reducing the polyolefinic nitrile to a corresponding polyolefinic amine.

In another aspect, the disclosure herein is directed to additive compositions comprising, or consisting essentially of, polyolefinic amines having an average molecular weight of at least 250 produced by a reaction comprising contacting an olefin or a polyolefin with an azo compound under free radical conditions to form a polyolefinic nitrile having an average molecular weight of at least 250, followed by reducing the polyolefinic nitrile to a corresponding polyolefinic amine.

In yet another aspect, the disclosure herein is directed to concentrate compositions comprising, or consisting essentially of, polyolefinic amines having an average molecular weight of at least 250 produced by a reaction comprising contacting an olefin or a polyolefin with an azo compound under free radical conditions to form a polyolefinic nitrile having an average molecular weight of at least 250, followed by reducing the polyolefinic nitrile to a corresponding polyolefinic amine.

In still yet another aspect, the disclosure herein is directed to a method of providing a detergent that comprises, or consists essentially of, polyolefinic amines having an average molecular weight of at least 250 produced by a reaction comprising contacting an olefin or a polyolefin with an azo compound under free radical conditions to form a polyolefinic nitrile having an average molecular weight of at least 250, followed by reducing the polyolefinic nitrile to a corresponding polyolefinic amine.

In another aspect, the disclosure herein is directed to a method of preventing deposits in an engine comprising contacting the engine with a composition that comprises, or consists essentially of, polyolefinic amines having an average molecular weight of at least 250 produced by a reaction comprising contacting an olefin or a polyolefin with an azo compound under free radical conditions to form a polyolefinic nitrile having an average molecular weight of at least 250, followed by reducing the polyolefinic nitrile to a corresponding polyolefinic amine.

In yet another aspect, the disclosure herein is directed to a method of improving detergency comprising providing a composition comprising, or consisting essentially of, polyolefinic amines having an average molecular weight of at least 250 produced by a reaction comprising contacting an olefin or a polyolefin with an azo compound under free radical conditions to form a polyolefinic nitrile having an average molecular weight of at least 250, followed by reducing the polyolefinic nitrile to a corresponding polyolefinic amine.

In still yet another aspect, the disclosure herein is directed to a use of a composition comprising, or consisting essentially of, polyolefinic amines having an average molecular weight of at least 250 produced by a reaction comprising contacting an olefin or a polyolefin with an azo compound under free radical conditions to form a polyolefinic nitrile having an average molecular weight of at least 250, followed by reducing the polyolefinic nitrile to a corresponding polyolefinic amine.

In another aspect, the disclosure herein is directed to an engine comprising a composition that comprises, or consists essentially of, polyolefinic amines having an average molecular weight of at least 250 produced by a reaction comprising contacting an olefin or a polyolefin with an azo compound under free radical conditions to form a polyolefinic nitrile having an average molecular weight of at least 250, followed by reducing the polyolefinic nitrile to a corresponding polyolefinic amine.

DETAILED DESCRIPTION OF THE INVENTION

The present disclosure is directed to a process for producing polyolefinic amines having an average molecular weight of at least 250 comprising a reaction comprising contacting an olefin or a polyolefin with an azo compound under free radical conditions to form a polyolefinic nitrile having an average molecular weight of at least 250, followed by reducing the polyolefinic nitrile to a corresponding polyolefinic amine.

As used herein, the singular forms "a" or "an" or "the" include plural references unless the context clearly dictates otherwise. For example, reference to "an azo compound" includes a composition comprising only one azo compound, as well as a composition comprising a mixture of two or more azo compounds.

As used herein, the term "about" encompasses the range of experimental error that occurs in any measurement.

As used herein, the term "olefin" encompasses a single specified olefin or a mixture of one or more olefins.

As used herein, the term "polyolefin" encompasses a single specified polyolefin or a mixture of one or more polyolefins.

The reaction disclosed herein comprises contacting an olefin or a polyolefin with an azo compound under free radical conditions to form a polyolefinic nitrile having an average molecular weight of at least 250, followed by reducing the polyolefinic nitrile to a corresponding polyolefinic amine.

Azo Compounds

The azo compound that may be used in the reaction to yield a polyolefinic amine having an average molecular weight of at least 250 is any compound that induces production of a free radical. Suitable azo compounds also include diazo compounds that are degraded into free radicals upon exposure of the reaction to heat. Non-limiting examples of suitable azo compounds include 2,2'-azobisisobutyronitrile ("AIBN"), 2,2'-azobis(2-butanenitrile), 1,1'-azobis(cyclohexanecarbonitrile), 2-(t-butylazo)-2-cyanopropane, 2,2'-azobis[2-methyl-N-(1,1)-bis(hydroxymethyl)-2-hydroxyethyl]-propionamide, 2,2'-azobis(2-methyl-N-hydroxyethyl)propionamide, 2,2'-azobis(N,N'-dimethyleneisobutyramidine) dichloride, 2,2'-azobis(2-amidinopropane) dichloride, 2,2'-azobis(N,N'-dimethyleneisobutyramide), 2,2'-azobis(2-methyl-N-[1,1-bis(hydroxymethyl)-2-hydroxyethyl]propionamide), 2,2'-azobis(2-methyl-N-[1,1-bis(hydroxymethyl)ethyl] propionamide), 2,2'-azobis(2-methyl-N-(2-hydroxy-ethyl) propionamide), 2,2'-azobis(isobutyramide) dihydrate, azobutyronitrile, 2,2'-azobis-(4-methoxy-2,4-dimethylpentanenitrile), 2,2'-azobis-(2,4-dimethylpentanenitrile), 2,2'-azobis-(2-methylbutyronitrile), and 2,2'-azobis(4-methoxy-2,4-dimethylvaleronitrile). In one embodiment, the azo compound is 2,2'-azobisisobutyronitrile ("AIBN").

Olefins and Polyolefins

The olefin that may be contacted with the azo compound in the reaction described herein may be branched or unbranched. Optionally, the olefin may contain more than one double bond and may be substituted. The double bond of the olefin may be located between any two carbons of the olefin.

Non-limiting examples of suitable olefins include one or more of propene, butene, pentene, isobutene, styrene, hexene, heptene, octene, nonene, decene, undecene, dodecene, tridecene, hexadecene, tetradecene, pentadecene, heptadecene, nonadecene, octadecene, 1-octadecene, eicocene, 1-eicocene, 1-doeicocene, 1-tetraeicocene, 1-hexaeicocene, 1-octaeicocene, 1-triacontene. Additionally, suitable mixtures of olefins include, but are not limited to, blends of 1-octadecene/1-tetraeicocene, 1-eicocene/1-doeicocene/1-tetraeicocene, and 1-tetraeicocene/1-hexaeicocene/1-octaeicocene.

The polyolefin that is contacted with the azo compound in the reaction described herein to yield a polyolefinic nitrile may be branched or unbranched. The polyolefin may be a polymer of any of the olefins described above. For example, suitable polyolefins include, but are not limited to, one or more of polypropene, polybutene, polypentene, polyisobutene, polystyrene, polyhexene, polyheptene, polyoctene, polynonene, polydecene, polyundecene, polydodecene, polytridecene, polyhexadecene, polytetradecene, polypentadecene, polyheptadecene, polynonadecene, polyoctadecene, polyeicocene. In one embodiment, the polyolefin is polyisobutene.

Catalyst for the Reaction with the Azo Compound

Optionally, a catalyst may be included to facilitate the reaction between the olefin or the polyolefin and the azo compound. The catalyst that may be included in the reaction to facilitate the reaction between the olefin or the polyolefin and the azo compound is any catalyst that is soluble in the reaction solvents. Suitable catalysts include, but are not limited to, a naked cation catalyst, a borane, a carborane, a fulleride, a metallocene a lithium containing catalyst, such as a weakly solvated lithium cation or $LiCB_{11}(CH_3)_{12}$.

Non-limiting examples of suitable borane and carborane catalysts include 7,8-dicarbaundecaborane(13), undecahydrido-7,8-dimethyl-7,8-dicarbaundecaborane, dodecahydrido-1-phenyl-1,3-dicarbanonaborane, tri(butyl)ammonium undecahydrido-8-ethyl-7,9-dicarbaundecaborate, 4-carbanonaborane(14), bis(tri(butyl)ammonium)nonaborate, bis(tri(butyl)ammonium)undecaborate, bis(tri(butyl)ammonium)dodecaborate, bis(tri(butyl)ammonium)decachlorodecaborate, tri(butyl)ammonium 1-carbadecaborate, tri(butyl)ammonium 1-carbadodecaborate, tri(butyl)ammonium 1-trimethylsilyl-1-carbadecaborate, tri(butyl)ammonium bis(nonahydrido-1,3-dicarbanonaborato)cobaltate(III), tri(butyl)ammonium bis(undecahydrido-7,8-dicarbaundecaborato)ferrate(III).

A metallocene is a derivative of cyclopentadienylidene, a metal derivative containing at least one cyclopentadienyl component bonded to a transition metal. Examples of suitable metallocenes are those derived from Group 3, 4 and 5 metals (Periodic Table as recently set forth by the IUPAC and ACS nomenclature committees), such as titanium, zirconium, hafnium, chromium, vanadium, scandium, yttrium, niobium, and tantalum.

Other exemplary catalysts for the reaction between the olefin or the polyolefin and the azo compound include, but are not limited to, cobalt, chromium, sodium, potassium, magnesium, calcium, beryllium, rubidium, strontium, aluminum or iron containing catalysts.

Catalyst for the Reduction Reaction

Optionally, a catalyst may be included to facilitate the reduction reaction in which the polyolefinic nitrile is reduced to the corresponding polyolefinic amine. The catalyst that may be included in the reaction to facilitate the reaction in which the polyolefinic nitrile with an average molecular weight of at least 250 is reduced to yield the corresponding polyolefinic amine is any catalyst that facilitates such a reaction. Suitable catalysts include, but are not limited to hydrogenation catalysts. Examples of suitable hydrogenation catalysts include, but are not limited to Raney nickel, palladium, platinum, cobalt, copper, copper oxide, Lindlar catalyst, rhodium, platinum dioxide, sodium borohydride, nickel, ruthenium, iron, tellurium, copper triphenylphosphine complexes, ruthenium phosphine complexes, rhodium carbonyl clusters, palladium on carbon, and complexes of palladium with quinoline, pyridine, and phenylisocyano ligands.

The reaction between the olefin or the polyolefin and the azo compound and the reduction reaction in which the polyolefinic nitrile is reduced to the corresponding polyolefinic amine may occur in the same solvent or different solvents. In one embodiment, the reaction between the olefin or the polyolefin and the azo compound occurs in one solvent and the polyolefinic nitrile of the desired molecular weight is isolated prior to the reduction of the polyolefinic nitrile to the corresponding polyolefinic amine. In another embodiment, the polyolefinic nitrile is not isolated and the reduction of the polyolefinic nitrile to the corresponding polyolefinic amine occurs in the same solvent as the reaction between the olefin or the polyolefin and the azo compound.

An exemplary reaction mechanism for producing polyolefinic amines from isobutene utilizing AIBN as the free radical initiator is shown below in Scheme I, wherein n is 0 to about 15,000.

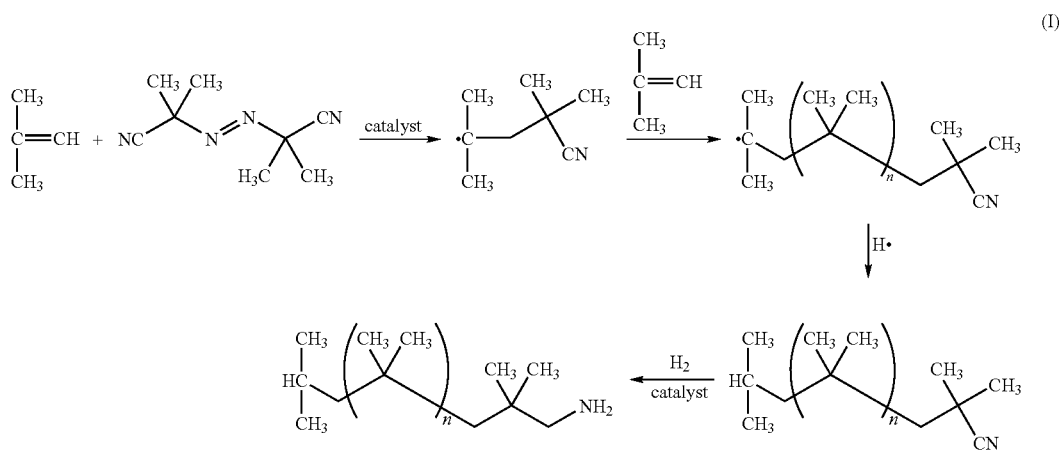

(I)

An exemplary reaction mechanism for producing polyolefinic amines from polyisobutyene utilizing AIBN as the free radical initiator is shown below in Scheme II, wherein n is 2 to about 15,000.

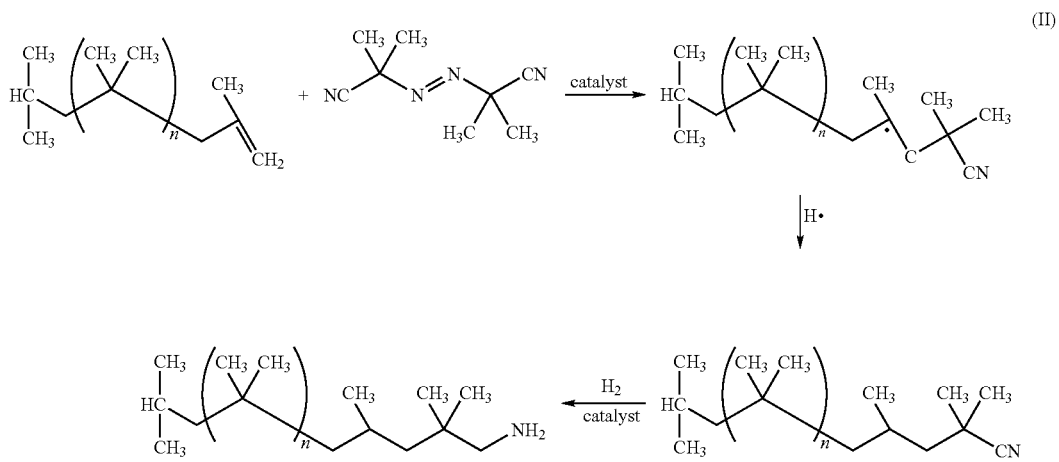

(II)

The ratio of azo compound to olefin or polyolefin may be adjusted to achieve a polyolefinic amine of the desired average molecular weight. For example, the mole ratio of the azo compound reactant to double bonds within the olefins or polyolefins may be at least about 1:1 or greater. For example, the mole ratio of the azo compound reactant to double bonds within the olefin or the polyolefin may be at least about 1:1 to about 1:200.

If the olefin or the polyolefin contains more than one double bond, the ratio of the azo compound and the olefin or the polyolefin may be adjusted such that only one nitrile group per molecule is formed. Alternatively, the ratio of the azo compound to the olefin or the polyolefin may be adjusted such that more than one nitrile group per molecule is formed.

The amount of catalyst that may be included to facilitate the reaction between the olefin or the polyolefin and the azo compound may be optimized for the reaction conditions utilized. Additionally, the amount of catalyst that may be included to facilitate the reduction reaction in which the polyolefinic nitrile is reduced to the polyolefinic amine may be optimized for the reaction conditions utilized.

The polyolefinic amines produced by the reaction described herein have an average molecular weight of at least about 250. In one embodiment, the polyolefinic amines produced by the reaction described herein have an average molecular weight of about 250 to about 200,000. In another embodiment, the polyolefinic amines produced by the reaction described herein have an average molecular weight of about 500 to about 150,000. In yet another embodiment, the polyolefinic amines produced by the reaction described herein have an average molecular weight of about 750 to about 100,000. In still yet another embodiment, the polyolefinic amines produced by the reaction described herein have an average molecular weight of about 1000 to about 75,000. In another embodiment, the polyolefinic amines produced by the reaction described herein have an average molecular weight of about 2500 to about 50,000. In yet another embodiment, the polyolefinic amines produced by the reaction described herein have an average molecular weight of about 5,000 to about 25,000. In still yet another embodiment, the polyolefinic amines produced by the reaction described herein have an average molecular weight of about 250 to about 10,000. In another embodiment, the polyolefinic amines produced by the reaction described herein have an average molecular weight of about 500 to about 5000. In yet another embodiment, the polyolefinic amines produced by the reaction described herein have an average molecular weight of about 750 to 2000.

The average number of carbon atoms per molecule of the polyolefinic amines produced by the reaction described herein is at least about 12. In one embodiment, the average number of carbon atoms per molecule of the polyolefinic amines produced by the reaction described herein is about 12 to about 15,000. In another embodiment, the average number of carbon atoms per molecule of the polyolefinic amines produced by the reaction described herein is about 12 to about 10,000. In yet another embodiment, the average number of carbon atoms per molecule of the polyolefinic amines produced by the reaction described herein is about 12 to about 7500. In still yet another embodiment, the average number of carbon atoms per molecule of the polyolefinic amines produced by the reaction described herein is about 12 to about 5000. In another embodiment, the average number of carbon atoms per molecule of the polyolefinic amines produced by the reaction described herein is about 12 to about 2500. In yet another embodiment, the average number of carbon atoms per molecule of the polyolefinic amines produced by the reaction described herein is about 12 to about 1000. In another embodiment, the average number of carbon atoms per molecule of the polyolefinic amines produced by the reaction described herein is about 12 to about 700. In yet another embodiment, the average number of carbon atoms per molecule of the polyolefinic amines produced by the reaction described herein is about 20 to about 600. In still yet another embodiment, the average number of carbon atoms per molecule of the polyolefinic amines produced by the reaction described herein is about 25 to about 500. In another embodiment, the average number of carbon atoms per molecule of the polyolefinic amines produced by the reaction described herein is about 50 to about 400. In yet another embodiment, the average number of carbon atoms per molecule of the polyolefinic amines produced by the reaction described herein is about 75 to about 300. In still yet another embodiment, the average number of carbon atoms per molecule of the polyolefinic amines produced by the reaction described herein is about 100 to about 200.

In one embodiment, the polyolefinic amine produced by the reaction described herein contains greater than about 35%, by weight of total polyolefin amine molecules, polyolefin amine molecules with at least 12 carbon atoms per molecule. In another embodiment, the polyolefinic amine produced by the reaction described herein contains greater than about 50%, by weight of total polyolefin amine molecules, polyolefin amine molecules with at least 12 carbon atoms per molecule. In yet another embodiment, the polyolefinic amine produced by the reaction described herein contains greater than about 75%, by weight of total polyolefin amine molecules, polyolefin amine molecules with at least 12 carbon atoms per molecule. In still yet another embodiment, the polyolefinic amine produced by the reaction described herein contains greater than about 90%, by weight of total polyolefin amine molecules, polyolefin amine molecules with at least 12 carbon atoms per molecule.

In one embodiment, the polyolefinic amine produced by the reaction described herein contains greater than about 35%, by weight of total polyolefin amine molecules, polyolefin amine molecules with at least 20 carbon atoms per molecule. In another embodiment, the polyolefinic amine produced by the reaction described herein contains greater than about 50%, by weight of total polyolefin amine molecules, polyolefin amine molecules with at least 20 carbon atoms per molecule. In yet another embodiment, the polyolefinic amine produced by the reaction described herein contains greater than about 75%, by weight of total polyolefin amine molecules, polyolefin amine molecules with at least 20 carbon atoms per molecule. In still yet another embodiment, the polyolefinic amine produced by the reaction described herein contains greater than about 90%, by weight of total polyolefin amine molecules, polyolefin amine molecules with at least 20 carbon atoms per molecule.

In one embodiment, the polyolefinic amine produced by the reaction described herein contains greater than about 35%, by weight of total polyolefin amine molecules, polyolefin amine molecules with at least 25 carbon atoms per molecule. In another embodiment, the polyolefinic amine produced by the reaction described herein contains greater than about 50%, by weight of total polyolefin amine molecules, polyolefin amine molecules with at least 25 carbon atoms per molecule. In yet another embodiment, the polyolefinic amine produced by the reaction described herein contains greater than about 75%, by weight of total polyolefin amine molecules, polyolefin amine molecules with at least 25 carbon atoms per molecule. In still yet another embodiment, the polyolefinic amine produced by the reaction described herein contains greater than about 90%, by weight of total polyolefin amine molecules, polyolefin amine molecules with at least 25 carbon atoms per molecule.

In one embodiment, the polyolefinic amine produced by the reaction described herein contains greater than about 35%, by weight of total polyolefin amine molecules, polyolefin amine molecules with at least 50 carbon atoms per molecule. In another embodiment, the polyolefinic amine produced by the reaction described herein contains greater than about 50%, by weight of total polyolefin amine molecules, polyolefin amine molecules with at least 50 carbon atoms per molecule. In yet another embodiment, the polyolefinic amine produced by the reaction described herein contains greater than about 75%, by weight of total polyolefin amine molecules, polyolefin amine molecules with at least 50 carbon atoms per molecule. In still yet another embodiment, the polyolefinic amine produced by the reaction described herein contains greater than about 90%, by weight of total polyolefin amine molecules, polyolefin amine molecules with at least 50 carbon atoms per molecule.

In one embodiment, the polyolefinic amine produced by the reaction described herein contains greater than about 35%, by weight of total polyolefin amine molecules, polyolefin amine molecules with at least 100 carbon atoms per molecule. In another embodiment, the polyolefinic amine produced by the reaction described herein contains greater than about 50%, by weight of total polyolefin amine molecules, polyolefin amine molecules with at least 100 carbon atoms per molecule. In yet another embodiment, the polyolefinic amine produced by the reaction described herein contains greater than about 75%, by weight of total polyolefin amine molecules, polyolefin amine molecules with at least 100 carbon atoms per molecule. In still yet another embodiment, the polyolefinic amine produced by the reaction described herein contains greater than about 90%, by weight of total polyolefin amine molecules, polyolefin amine molecules with at least 100 carbon atoms per molecule.

In one embodiment, the polyolefinic amine produced by the reaction described herein contains greater than about 35%, by weight of total polyolefin amine molecules, polyolefin amine molecules with at least 250 carbon atoms per molecule. In another embodiment, the polyolefinic amine produced by the reaction described herein contains greater than about 50%, by weight of total polyolefin amine molecules, polyolefin amine molecules with at least 250 carbon atoms per molecule. In yet another embodiment, the polyolefinic amine produced by the reaction described herein contains greater than about 75%, by weight of total polyolefin amine molecules, polyolefin amine molecules with at least 250 carbon atoms per molecule. In still yet another embodiment, the polyolefinic amine produced by the reaction described herein contains greater than about 90%, by weight of total polyolefin amine molecules, polyolefin amine molecules with at least 250 carbon atoms per molecule.

In one embodiment, the polyolefinic amine produced by the reaction described herein contains greater than about 35%, by weight of total polyolefin amine molecules, polyolefin amine molecules with at least 500 carbon atoms per molecule. In another embodiment, the polyolefinic amine produced by the reaction described herein contains greater than about 50%, by weight of total polyolefin amine molecules, polyolefin amine molecules with at least 500 carbon atoms per molecule. In yet another embodiment, the polyolefinic amine produced by the reaction described herein contains greater than about 75%, by weight of total polyolefin amine molecules, polyolefin amine molecules with at least 500 carbon atoms per molecule. In still yet another embodiment, the polyolefinic amine produced by the reaction described herein contains greater than about 90%, by weight of total polyolefin amine molecules, polyolefin amine molecules with at least 500 carbon atoms per molecule.

In one embodiment, the polyolefinic amine produced by the reaction described herein contains greater than about 35%, by weight of total polyolefin amine molecules, polyolefin amine molecules with at least 700 carbon atoms per molecule. In another embodiment, the polyolefinic amine produced by the reaction described herein contains greater than about 50%, by weight of total polyolefin amine molecules, polyolefin amine molecules with at least 700 carbon atoms per molecule. In yet another embodiment, the polyolefinic amine produced by the reaction described herein contains greater than about 75%, by weight of total polyolefin amine molecules, polyolefin amine molecules with at least 700 carbon atoms per molecule. In still yet another embodiment, the polyolefinic amine produced by the reaction described herein contains greater than about 90%, by weight of total polyolefin amine molecules, polyolefin amine molecules with at least 700 carbon atoms per molecule.

In one embodiment, the polyolefinic amine produced by the reaction described herein contains greater than about 35%, by weight of total polyolefin amine molecules, polyolefin amine molecules with at least 1000 carbon atoms per molecule. In another embodiment, the polyolefinic amine produced by the reaction described herein contains greater than about 50%, by weight of total polyolefin amine molecules, polyolefin amine molecules with at least 1000 carbon atoms per molecule. In yet another embodiment, the polyolefinic amine produced by the reaction described herein contains greater than about 75%, by weight of total polyolefin amine molecules, polyolefin amine molecules with at least 1000 carbon atoms per molecule. In still yet another embodiment, the polyolefinic amine produced by the reaction described herein contains greater than about 90%, by weight of total polyolefin amine molecules, polyolefin amine molecules with at least 1000 carbon atoms per molecule.

In one embodiment, the polyolefinic amine produced by the reaction described herein contains greater than about 35%, by weight of total polyolefin amine molecules, polyolefin amine molecules with at least 2500 carbon atoms per molecule. In another embodiment, the polyolefinic amine produced by the reaction described herein contains greater than about 50%, by weight of total polyolefin amine molecules, polyolefin amine molecules with at least 2500 carbon atoms per molecule. In yet another embodiment, the polyolefinic amine produced by the reaction described herein contains greater than about 75%, by weight of total polyolefin amine molecules, polyolefin amine molecules with at least 2500 carbon atoms per molecule. In still yet another embodiment, the polyolefinic amine produced by the reaction described herein contains greater than about 90%, by weight of total polyolefin amine molecules, polyolefin amine molecules with at least 2500 carbon atoms per molecule.

In one embodiment, the polyolefinic amine produced by the reaction described herein contains greater than about 35%, by weight of total polyolefin amine molecules, polyolefin amine molecules with at least 5000 carbon atoms per molecule. In another embodiment, the polyolefinic amine produced by the reaction described herein contains greater than about 50%, by weight of total polyolefin amine molecules, polyolefin amine molecules with at least 5000 carbon atoms per molecule. In yet another embodiment, the polyolefinic amine produced by the reaction described herein contains greater than about 75%, by weight of total polyolefin amine molecules, polyolefin amine molecules with at least 5000 carbon atoms per molecule. In still yet another embodiment, the polyolefinic amine produced by the reaction described herein contains greater than about 90%, by weight of total polyolefin amine molecules, polyolefin amine molecules with at least 5000 carbon atoms per molecule.

In one embodiment, the polyolefinic amine produced by the reaction described herein contains greater than about 35%, by weight of total polyolefin amine molecules, polyolefin amine molecules with at least 7500 carbon atoms per molecule. In another embodiment, the polyolefinic amine produced by the reaction described herein contains greater than about 50%, by weight of total polyolefin amine molecules, polyolefin amine molecules with at least 7500 carbon atoms per molecule. In yet another embodiment, the polyolefinic amine produced by the reaction described herein contains greater than about 75%, by weight of total polyolefin amine molecules, polyolefin amine molecules with at least 7500 carbon atoms per molecule. In still yet another embodiment, the polyolefinic amine produced by the reaction described herein contains greater than about 90%, by weight of total polyolefin amine molecules, polyolefin amine molecules with at least 7500 carbon atoms per molecule.

In one embodiment, the polyolefinic amine produced by the reaction described herein contains greater than about 35%, by weight of total polyolefin amine molecules, polyolefin amine molecules with at least 10,000 carbon atoms per molecule. In another embodiment, the polyolefinic amine produced by the reaction described herein contains greater than about 50%, by weight of total polyolefin amine molecules, polyolefin amine molecules with at least 10,000 carbon atoms per molecule. In yet another embodiment, the polyolefinic amine produced by the reaction described herein contains greater than about 75%, by weight of total polyolefin amine molecules, polyolefin amine molecules with at least 10,000 carbon atoms per molecule. In still yet another embodiment, the polyolefinic amine produced by the reaction described herein contains greater than about 90%, by weight of total polyolefin amine molecules, polyolefin amine molecules with at least 10,000 carbon atoms per molecule.

In one embodiment, the polyolefinic amine produced by the reaction described herein is a mixture in which the predominant polyolefin amine molecule contains at least about 12 carbon atoms per molecule. In another embodiment, the polyolefinic amine produced by the reaction described herein is a mixture in which the predominant polyolefin amine molecule contains at least about 20 carbon atoms per molecule. In yet another embodiment, the polyolefinic amine produced by the reaction described herein is a mixture in which the predominant polyolefin amine molecule contains at least about 25 carbon atoms per molecule. In still yet another embodiment, the polyolefinic amine produced by the reaction described herein is a mixture in which the predominant polyolefin amine molecule contains at least about 50 carbon atoms per molecule. In another embodiment, the polyolefinic amine produced by the reaction described herein is a mixture in which the predominant polyolefin amine molecule contains at least about 75 carbon atoms per molecule. In yet another embodiment, the polyolefinic amine produced by the reaction described herein is a mixture in which the predominant polyolefin amine molecule contains at least about 100 carbon atoms per molecule. In still yet another embodiment, the polyolefinic amine produced by the reaction described herein is a mixture in which the predominant polyolefin amine molecule contains at least about 250 carbon atoms per molecule. In another embodiment, the polyolefinic amine produced by the reaction described herein is a mixture in which the predominant polyolefin amine molecule contains at least about 500 carbon atoms per molecule. In yet another embodiment, the polyolefinic amine produced by the reaction described herein is a mixture in which the predominant polyolefin amine molecule contains at least about 700 carbon atoms per molecule. In still yet another embodiment, the polyolefinic amine produced by the reaction described herein is a mixture in which the predominant polyolefin amine molecule contains at least about 1000 carbon atoms per molecule. In another embodiment, the polyolefinic amine produced by the reaction described herein is a mixture in which the predominant polyolefin amine molecule contains at least about 2500 carbon atoms per molecule. In yet another embodiment, the polyolefinic amine produced by the reaction described herein is a mixture in which the predominant polyolefin amine molecule contains at least about 5000 carbon atoms per molecule. In still yet another embodiment, the polyolefinic amine produced by the reaction described herein is a mixture in which the predominant polyolefin amine molecule contains at least about 7500 carbon atoms per molecule. In another embodiment, the polyolefinic amine produced by the reaction described herein is a mixture in which the predominant polyolefin amine molecule contains at least about 10,00 carbon atoms per molecule.

Compositions

The novel compositions of this invention contain polyolefinic amines having an average molecular weight of at least 250 produced by a reaction that comprises contacting an olefin or a polyolefin with an azo compound under free radical conditions. In one embodiment, polyolefinic amines having an average molecular weight of at least 250 produced by a reaction that comprises contacting an olefin or a polyolefin with an azo compound under free radical conditions are included in a fuel composition. In another embodiment, polyolefinic amines produced by a reaction that comprises contacting an olefin or a polyolefin with an azo compound under free radical conditions are included in an additive composition. In yet another embodiment, polyolefinic amines having an average molecular weight of at least 250 produced by a reaction that utilizes an azo compound as a free radical initiator and a catalyst are included in a concentrate composition.

Optionally, either the additive composition or concentrate composition may be added to a fuel composition before the fuel composition is contacted with the engine. Alternatively, either the additive composition or concentrate composition may be added to a fuel composition after the fuel composition is contacted with the engine.

In one embodiment, the fuel composition includes one or more hydrocarbon fuels. Suitable hydrocarbon fuels include, but are not limited to gasoline, middle distillate fuel, diesel, bio diesel, and kerosene.

When formulating a fuel composition of this invention, polyolefinic amines having an average molecular weight of at least 250 produced by the reaction described herein is employed in an amount sufficient to reduce or inhibit deposit formation in an engine. Thus, the fuel composition will contain a minor amount of polyolefinic amines produced by the reaction described herein.

In another embodiment, the fuel composition will contain, on an active ingredient basis, an amount of polyolefinic amines having an average molecular weight of at least 250 produced by the reaction described herein of about 10 to about 10,000 ppm (parts by weight of the reaction product per million parts by weight of fuel plus polyolefinic amine with an average molecular weight of at least 250). In yet another embodiment, the fuel composition will contain, on an active ingredient basis, about 50 to about 1000 ppm polyolefinic amines having an average molecular weight of at least 250 produced by the reaction described herein. In still yet another embodiment, the fuel composition will contain, on an active ingredient basis, about 100 to about 500 ppm polyolefinic amines having an average molecular weight of at least 250 produced by the reaction described herein.

In another embodiment, polyolefinic amines having an average molecular weight of at least 250 produced by the reaction described herein is formulated as an additive composition and may optionally be added to a fuel composition prior to contacting the engine with the fuel composition.

Optionally, the additive composition containing polyolefinic amines having an average molecular weight of at least 250 produced by the reaction described herein may be formulated with a carrier to yield a concentrate composition. In one embodiment, the carrier is a liquid carrier fluid.

Alternatively, the polyolefinic amines having an average molecular weight of at least 250 produced by the reaction described herein is formulated with a carrier to yield a concentrate composition. In one embodiment, the carrier is a liquid carrier fluid.

Typically, the additive composition contains about 30 to about 80 weight percent of polyolefinic amines having an average molecular weight of at least 250 produced by the reaction described herein. In one embodiment, the additive composition contains about 50 to about 70 weight percent of polyolefinic amines having an average molecular weight of at least 250 produced by the reaction described herein.

In one embodiment, the additive composition may be diluted with about 20 to about 70 weight percent of a carrier to yield a concentrate composition. In another embodiment, the additive composition may be diluted with about 30 to about 50 weight percent of a liquid carrier to yield a concentrate composition.

In general, the weight ratio of carrier to the additive composition containing polyolefinic amines having an average molecular weight of at least 250 produced by the reaction described herein, on an active ingredient basis, will usually be about 0.3:1 to about 2:1. In one embodiment, the weight ratio of carrier to the additive composition containing polyolefinic amines having an average molecular weight of at least 250 produced by the reaction described herein, on an average ingredient basis, will usually be about 0.5:1 to about 1:1. The active ingredient basis excludes the weight of (i) any olefin or polyolefin molecules associated with, and remaining, in the additive composition, and (ii) solvent(s), if any, used in the manufacture of the additive composition, either during or after its formation but before addition of the carrier.

The proportion of the carrier used relative to the additive composition containing polyolefinic amines having an average molecular weight of at least 250 produced by the reaction described herein, is such that the fuel composition containing the diluted additive composition, when consumed in an engine, results in improved cleanliness as compared to cleanliness of the same engine operated on the same fuel composition except for being devoid of the additive composition.

In addition to polyolefinic amines having an average molecular weight of at least 250 produced by the reaction described herein, the fuel compositions, additive compositions, and/or concentrate compositions may optionally contain additional components. For example, the fuel compositions, additive compositions, and/or concentrate compositions may include one or more of combustion improvers, cetane improvers, friction modifiers, detergents, dispersants, antioxidants, heat stabilizers, corrosion inhibitors, dehazers, metal deactivators, antifoaming agents, cosolvents, package compatibilisers, lubricity additives, antistatic additives, scavengers, pollution suppressants, cold flow improvers, demulsifiers, and the like. Similarly, the fuel compositions, additive compositions, and/or concentrate compositions may contain suitable amounts of conventional fuel blending components such as methanol, ethanol, dialkyl ethers, and the like.

Any of the additional components can be blended with polyolefinic amines having an average molecular weight of at least 250 produced by the reaction described herein into a fuel composition, an additive composition, or a concentrate composition individually or in various sub-combinations. In one embodiment, two or more components to be included in the final fuel composition are blended concurrently using an additive composition. In another embodiment, the additive composition is diluted with a carrier to yield a concentrate composition which may be added to the fuel composition.

This invention is applicable to the operation of engines (e.g., engines used in electrical power generation installations, in pumping stations, engines used as prime movers in automobiles, trucks, road-grading equipment, military vehicles, etc.). Accordingly, one embodiment of the invention includes a method for reducing the amount of deposits of an engine which comprises contacting the engine with a fuel composition comprising a major amount of a hydrocarbon fuel and a minor portion of a composition containing polyolefinic amines having an average molecular weight of at least 250 produced by the reaction described herein.

Another embodiment of the invention includes a method for improving detergency which comprises utilizing a composition containing polyolefinic amines having an average molecular weight of at least 250 produced by the reaction described herein.

Another embodiment of the invention includes the use of a composition containing polyolefinic amines having an average molecular weight of at least 250 produced by the reaction described herein. In one embodiment, the use of the composition is as a detergent. In another embodiment, the use of the composition is to reduce the amount of deposits in an engine.

In some embodiments, the reaction described herein may occur in the carrier liquid. In other instances, polyolefinic amines having an average molecular weight of at least 250 produced by the reaction described herein is blended with a suitable amount of a carrier liquid. If desired, the reaction described herein to yield polyolefinic amines having an average molecular weight of at least 250 may be performed in a suitable solvent or carrier liquid and then blended with an additional quantity of the same or different carrier liquid.

The following examples are illustrative, but not limiting, of the reactions of the present invention. Other suitable modifications and adaptations of the variety of conditions and parameters normally encountered in the field, and which are obvious to those skilled in the art, are within the spirit and scope of the invention.

All patents and publications cited herein are fully incorporated by reference herein in their entirety.

EXAMPLES

Example 1

Synthesis of Polyisobutylene Amine Using Isobutene as the Starting Material

Isobutene will be combined with AIBN in the presence of a lithium containing catalyst, such as $LiCB_{11}(CH_3)_{12}$. The isobutene and AIBN will be reacted at a suitable molar ratio to achieve a polyolefinic nitrile of a desired average molecular weight.

The polyolefinic nitrile of the desired average molecular weight will then be isolated and contacted with a suitable catalyst to yield a polyolefinic amine of a desired molecular weight.

Example 2

Synthesis of Polyisobutylene Amine Using Polyisobutene as the Starting Material

Polyisobutene of a specific average molecular will be combined with AIBN in the presence of a lithium containing catalyst, such as $LiCB_{11}(CH_3)_{12}$. The polyisobutene and AIBN will be reacted at a suitable molar ratio to achieve the desired polyolefinic nitrile.

The desired polyolefinic nitrile will then be isolated and contacted with a suitable catalyst to yield the desired polyolefinic amine.

What is claimed is:

1. A reaction, comprising reacting an olefin or a polyolefin with an azo compound to form a polyolefinic nitrile having an average molecular weight of at least 250, wherein said reaction further comprises reducing said polyolefinic nitrile to a corresponding polyolefinic amine.

2. The reaction of claim 1, wherein reducing said polyolefinic nitrile to a corresponding polyolefinic amine occurs in the presence of a hydrogenation catalyst.

3. The reaction of claim 2, wherein said hydrogenation catalyst is selected from a group consisting of Raney nickel, palladium, platinum, cobalt, copper, copper oxide, Lindlar catalyst, rhodium, platinum dioxide, sodium borohydride, nickel, ruthenium, iron, tellurium, copper triphenylphosphine complexes, ruthenium phosphine complexes, rhodium carbonyl clusters, palladium on carbon, and complexes of palladium with quinoline, pyridine, and phenylisocyano ligands.

4. The reaction of claim 1, wherein said polyolefinic amine contains an average number of carbon atoms of at least about 12.

5. The reaction of claim 1, wherein said polyolefinic amine contains greater than about 35%, by weight of total polyolefin amine molecules, polyolefin amine molecules with at least 12 carbon atoms.

6. The reaction of claim 1, wherein said polyolefinic amine is a mixture in which the predominant polyolefin amine molecule contains at least about 12 carbon atoms per molecule.

7. A composition comprising at least one polyolefinic amine produced by the reaction of claim 1.

8. The composition of claim 7, wherein the composition additionally contains one or more additives selected from the group consisting of combustion improvers, cetane improvers, friction modifiers, detergents, dispersants, antioxidants, heat stabilizers, corrosion inhibitors, dehazers, metal deactivators, antifoaming agents, cosolvents, package compatibilisers, lubricity additives, antistatic additives, scavengers, pollution suppressants, cold flow improvers, and demulsifiers.

9. A fuel composition comprising at least one polyolefinic amine produced by the reaction of claim 1 in a minor amount and a major amount of a hydrocarbon fuel.

10. The fuel composition of claim 9, wherein said polyolefinic amine produced by the reaction of claim 1 is present in an amount that is about 10 to about 10,000 parts per million.

11. The fuel composition of claim 10, wherein said fuel composition additionally contains one or more additives selected from the group consisting of combustion improvers, cetane improvers, friction modifiers, detergents, dispersants, antioxidants, heat stabilizers, corrosion inhibitors, dehazers, metal deactivators, antifoaming agents, cosolvents, package compatibilisers, lubricity additives, antistatic additives, scavengers, pollution suppressants, cold flow improvers, and demulsifiers.

12. A method for improving detergency comprising providing a composition that comprises at least one polyolefinic amine produced by the reaction of claim 1.

13. A method of preventing deposits in an engine comprising contacting the engine with a composition that comprises at least one polyolefinic amine produced by the reaction of claim 1.

14. The reaction of claim 1, wherein the azo compound is selected from the group consisting of 2,2'-azobisisobutyronitrile ("AIBN"), 2,2' azobis(2-butanenitrile), 1,1'-azobis(cyclohexanecarbonitrile), 2-(tbutylazo)-2cyanopropane, 2,2'-azobis[2-methyl-N-(1,1)bis(hydroxymethyl)-2hydroxyethyl]-propionamide, 2,2'-azobis(2-methyl-Nhydroxyethyl)propionamide, 2,2'-azobis(N,N'-dimethyleneisobutyramidine) dichloride, 2,2'-azobis (2amidinopropane) dichloride, 2,2'-azobis(N,N' dimethyleneisobutyramide), 2,2'-azobis(2-methyl-N-[1,1-bis(hydroxymethyl)-2-hydroxyethyl]propionamide), 2,2'-azobis(2-methylN-[1,1-bis(hydroxymethyl)ethyl]propionamide), 2,2'-azobis(2-methylN-(2-hydroxy-ethyl) propionamide), 2,2' azobis(isobutyramide) dihydrate, azobutyronitrile, 2,2'-azobis-(4-methoxy-2,4-dimethylpentanenitrile), 2,2'-azobis-(2,4-dimethylpentanenitrile), 2,2'-azobis-(2-methylbutyronitrile), 2,2' azobis(4-methoxy-2,4-dimethylvaleronitrile).

15. The reaction of claim 14, wherein the azo compound is 2,2'-azobisisobutyronitrile.

16. The reaction of claim 1, wherein the ratio of the azo to olefin or polyolefin is about 1:1.

17. The reaction of claim 1, wherein the ratio of azo to olefin or polyolefin is greater than about 1:1.

18. The reaction of claim 1, wherein the polyolefinic nitrile has more than one nitrile group per polyolefin amine.

* * * * *